United States Patent [19]

O'Neal

[11] 4,170,462

[45] Oct. 9, 1979

[54] METHOD FOR CONTROLLING THE RELATIVE STEM GROWTH OF PLANTS

[75] Inventor: Thomas D. O'Neal, Princeton, N.J.

[73] Assignee: American Cyanamid Company, Stamford, Conn.

[21] Appl. No.: 871,874

[22] Filed: Jan. 23, 1978

[51] Int. Cl.² ............................................. A01N 5/00
[52] U.S. Cl. ......................................... 71/76; 71/78; 548/301
[58] Field of Search ..................... 71/76, 92; 548/301

[56] References Cited

U.S. PATENT DOCUMENTS

| | | | |
|---|---|---|---|
| 3,068,239 | 12/1962 | Miller | 71/92 |
| 3,133,079 | 5/1964 | Luckenbaugh | 71/92 |
| 3,361,752 | 1/1968 | D'Amico | 71/92 |
| 3,428,646 | 2/1969 | Hellerbach | 548/301 |
| 3,551,417 | 12/1970 | Symon et al. | 71/92 |
| 3,717,659 | 2/1973 | Sarett et al. | 548/301 |
| 3,922,158 | 11/1975 | Martin et al. | 71/76 |
| 3,923,495 | 12/1975 | Alt et al. | 71/76 |
| 3,947,263 | 3/1976 | Brouwer et al. | 71/76 |
| 3,968,120 | 7/1976 | Regel et al. | 71/92 |
| 4,055,409 | 10/1977 | Johnson et al. | 71/92 |

*Primary Examiner*—Glennon H. Hollrah
*Attorney, Agent, or Firm*—H. G. Jackson

[57] ABSTRACT

This invention relates to a method for controlling the relative stem and/or axillary growth of plants by applying to the foliage of the plants, to soil containing seeds of the plants, or to soil in which the plants are growing, a plant-growth regulating amount of an imidazolinyl benzoic acid, ester or salt.

9 Claims, No Drawings

METHOD FOR CONTROLLING THE RELATIVE STEM GROWTH OF PLANTS

The invention relates to a method for controlling plant growth by applying to the foliage thereof, to soil containing seeds of the plants, or to soil in which the plants are growing, plant-growth-regulating amount of a compound of the formula:

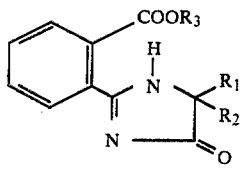

wherein $R_1$ is alkyl $C_1-C_4$; $R_2$ is alkyl $C_1-C_6$, cycloalkyl $C_3-C_6$, alkenyl $C_2-C_4$, or when $R_1$ and $R_2$ are taken together with the carbon to which they are attached they may represent cycloalkyl $C_3-C_6$ optionally substituted with methyl; $R_3$ is hydrogen, alkyl $C_1-C_{12}$, alkenyl $C_3-C_5$ optionally substituted with one halogen substituent, preferably chlorine, or one or two methyl substituents, alkynyl $C_3-C_5$ optionally substituted with one halogen substituent, preferably chlorine, or one or two methyl substituents, benzyl, cyclohexenylmethyl, pentadienyl, or a salt-forming cation selected from the group consisting of alkali metals, ammonium and aliphatic ammonium; and except where $R_3$ is a salt forming cation, the acid addition salts thereof.

The "aliphatic ammonium" refers to an aliphatic ammonium group selected from the group consisting of monoalkylammonium, dialkylammonium, trialkylammonium, monoalkenylammonium, dialkenylammonium, trialkenylammonium, monoalkylammonium, dialkynylammonium, trialkynylammonium, monoalkanolammonium, dialkanolammonium, trialkanolammonium, said aliphatic ammonium group containing a total of from 1 to 18 carbon atoms.

The compounds of the present invention and their use as herbicides is disclosed and claimed in copending, coassigned, U.S. Ser. No. 822,458, filed Aug. 8, 1977 now abandoned, in the name of Marinus Los.

Preferred compounds for use as plant growth regulating agents, particularly dwarfing agents for crop plants, and axillary growth inhibitors for solanaceous, herbaceous and wood plant species, are those represented by formula I above, wherein $R_1$ is alkyl $C_1-C_3$; $R_2$ is alkyl $C_1-C_3$, and when $R_1$ and $R_2$ are taken together with the carbon to which they are attached they represent cyclohexyl; $R_3$ is alkyl $C_1-C_{12}$, alkenyl $C_3-C_5$ optionally substituted with one chlorine substituent or one or two methyl substituents, alkynyl $C_3-C_5$ optionally substituted with a methyl substituent, benzyl, cyclohexenylmethyl or pentadienyl, and the acid addition salts thereof.

Still more preferred formula I compounds are those wherein $R_1$ is methyl, $R_2$ is isopropyl, and $R_3$ is as described immediately above.

In accordance with this invention, formula I imidazolinyl benzoates where $R_3$ is substituent other than hydrogen, alkali metal, ammonium or aliphatic ammonium, can be prepared by reacting an imidazoisoindoledione represented by formula II below with an appropriate alkali metal alkoxide. The reaction is preferably conducted under a blanket of inert gas at a temperature between 20° C. and 50° C. Generally, an alkali metal or alkali metal hydride is mixed with an appropriate alcohol and the mixture then admixed with the imidazoisoindoledione II.

Among the inert gases which may be used to blanket these reactions are nitrogen, argon and helium; but nitrogen is preferred.

Alkali metals and alkali metal hydrides which may be used include sodium, sodium hydride, potassium, potassium hydride, lithium and lithium hydride.

These reactions may be graphically illustrated as follows:

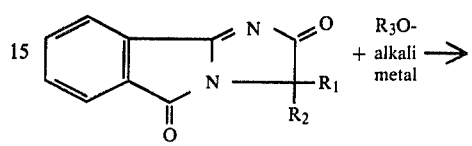

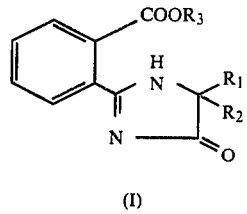

wherein $R_1$, $R_2$ and $R_3$ are as described above.

In these reactions, the alcohol functions as both reactant and solvent. As such, a secondary solvent is not required; however, when an expensive alcohol is used in the reaction and/or a large excess of alcohol would normally be required to provide optimum reaction conditions, it may be desirable to add a less expensive secondary solvent such as dioxane, tetrahydrofuran or other non-protic solvent, to the reaction mixture. The amount of non-protic solvent added to the reaction mixture may be widely varied however, it generally will not exceed fourfold the amount of alcohol used. Thus, the ratio of secondary solvent to alcohol, which may be employed in the process of the present invention, is from about 0.0:1 to 4.0:1.

It should also be understood that the imidazolinyl benzoates represented by formula I above, may be tautomeric. While, for convenience, they are depicted by a single structure identified as formula I, they may exist in either of the isomeric forms illustrated as follows:

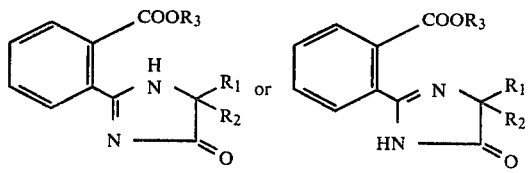

wherein $R_1$, $R_2$ and $R_3$ are as described. As such, both isomeric forms of the imidazolinyl benzoates are meant to be included under the formula I definition.

These compounds are amphoteric. They will dissolve in both acidic and basic aqueous solutions and when treated with strong acids, particularly strong mineral acids such as hydrochloric acid, sulfuric acid or hydrobromic acid, will form the acid addition salts of the imidazolinyl benzoates I.

It should also be understood that when $R_1$ and $R_2$ represent different groups on the imidazolinyl benzoates, depicted by formula I, the carbon atom to which they are attached is an asymmetric carbon atom. Therefore, the products (as well as their intermediates) exist in d- and l- forms as well as dl- forms.

Preparation of the d- or the l- form is thus readily obtained by reacting the appropriate optically active d- or l- imidazoisoindoledione II with the appropriate alcohol III to obtain the corresponding d- or l- imidazolinyl benzoate I.

The formula II imidazoisoindoledioness which are used as intermediates for the preparation of the imidazolinyl benzoates of this invention are described in the U.S. Pat. No. 4,017,510, issued Apr. 12, 1977, application Ser. No. 631,357, filed Nov. 12, 1975, and incorporated herein by reference thereto.

Formula I compounds wherein $R_3$ is hydrogen and $R_1$ and $R_2$ are as described above, can be prepared by reacting a formula II imidazoisoindoledione with an excess of hydrochloric acid in the presence of a water-miscible solvent such as tetrahydrofuran or dioxane. This reaction yields the formula IV lactone hydrochloride which, when treated with one equivalent of base such as sodium hydroxide, potassium hydroxide or sodium carbonate, yields the corresponding acid. This reaction can be illustrated as follows:

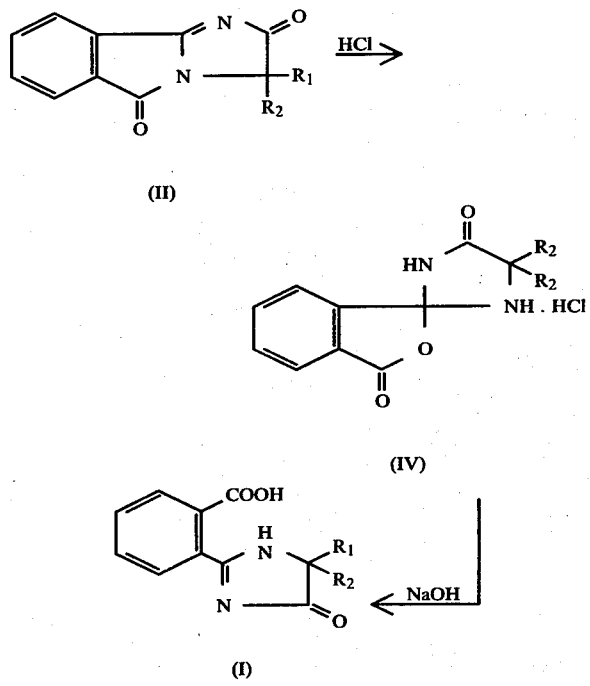

The thus-formed imidazolinyl acid can then be converted to the corresponding alkali metal, ammonium or aliphatic ammonium salt.

Where the alkali metal salt is desired, said acid is treated with a concentrated aqueous solution of the alkali metal hydroxide, followed by removal of the water, preferably through azeotropic distillation with an organic solvent such as dioxane.

The ammonium or aliphatic ammonium salts can be prepared in similar fashion excepting that the formula I acid is partially dissolved in a lower alcohol such as methanol, ethanol, isopropanol, or the like, and the thus-formed solution treated with ammonia or the appropriate aliphatic amine. Thereafter, the reaction mixture is concentrated and the remaining solid treated with hexane and then dried to recover the ammonium or aliphatic ammonium formula I salt.

The aliphatic ammonium salts of the compounds of the invention are prepared from organic amines having a molecular weight below about 300. These amines include methylamine, ethylamine, n-propylamine, isopropylamine, n-butylamine, isobutylamine, sec-butylamine, n-amylamine, iso-amylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, di-heptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3,-dimethylbutenyl-2-amine, di-butenyl-2-amine, n-hexenyl-2-amine and propylenediamine.

The compounds of the present invention are highly effective plant growth regulating agents. They may be used effectively for controlling the relative stem and/or axillary growth of both monocotyledonous and dicotyledonous plants by application thereof to the foliage, stems, roots or seeds of the plants, or by application to soil in which the plants are grown. Generally, one treatment is effective on the total growth of the plant; however, repeated treatments may be made when desired.

The most characteristic growth alterations brought about by the treatment of plants, particularly crop plants, with the compounds of this invention, are shorter thicker stems and reduction in (axillary) growth. As such, the formula I compounds of the present invention are particularly useful for dwarfing (i.e. reducing the relative stem growth) of graminaceous crops such as, barley, oats, wheat, rice and corn, and preventing lodging thereof. Surprisingly, the compounds of the invention are also effective for reducing the relative stem growth of leguminous crops, particularly the bean producing varieties, such as snapbeans, soybeans, greenbeans, and limabeans. Usually about 0.0002 to 4.48 kg/hectare and preferably 0.11 to 2.24 kg/hectare of the formula I compound is effective for achieving this dwarfing effect.

The plant growth regulating effects of the compounds of the present invention is further demonstrated by the compounds' usefulness for controlling axillary growth of herbaceous and woody plant species, such as tobacco plants and coffee trees, to produce a more desirable plant growth. For control of axillary growth on coffee trees the trunks of the trees are generally treated, by spraying or painting, with active imidazolinyl benzoate I. In practice this can amount to about 0.5 to 2.860 kg/hectare of active ingredient. It is also found that solutions and/or suspensions, preferably aqueous, containing from about 1 mg to 150 mg, and preferably 1 to 40 mg per plant of active compound applied to the foliage of the plant, or 85 to 120 mg per plant applied to the soil in which it is growing, is effective for inhibiting sucker growth on mechanically topped tobacco plants. In practice, generally about 0.5 to 2.0 kg per hectare of active ingredient is used.

In tobacco farming, maturation of the crop for harvesting is initiated by removal of the apical flower growth of the tobacco plant in a process known as "topping". This process facilitates the development of large leaves which form the commercial crop. Their development, however, is offset by the enhanced development of lateral (axillary) buds. The lateral growth (called "sucker growth") again reduces the nutrient supply available for large leaf development. Thus it is essential to control sucker growth on the tobacco plants if optimal production of marketable leaves is to be achieved.

Control of axilllary growth may be accomplished by applying a bud growth inhibiting amount of the active compound to the foliage of the topped tobacco or to the soil in which it is growing.

The imidazolinyl benzoates (I) of the present invention exhibit very limited solubility in water, as such, they are generally formulated as wettable powders, emulsifiable concentrates, or flowable liquids which are usually dispersed in water or other inexpensive liquid diluent for application as a liquid spray. The compounds of the invention may also be prepared as granular formulations containing, generally, about 5% to 15% by weight of toxicant.

Typically, a wettable powder can be prepared by grinding together about 25% to 80% by weight of the imidazolinyl benzoate, about 2% to 5% by weight of a surfactant such as sodium N-methyl-N-oleoyl taurate, alkyl phenoxy polyoxyethylene ethanol, or sodium alkyl naphthalene sulfonate, 5% to 10% by weight of a dispersing agent such as a highly purified sodium lignosulfonate and 25% to 63% by weight of a finely divided carrier such as kaolin, attapulgite, diatomaceous earth, or the like.

A typical formulation prepared in accordance with the above description is as follows:

50% by weight of 1-methyl-2-propynyl 0-(5-isopropyl-5-methyl-4-oxo-2-imidazolin-2-yl) benzoic acid ester, 3% by weight of sodium N-methyl-N-oleoyl taurate, 10% by weight of sodium lignosulfonate, and 37% by weight of kaolin.

Flowable liquid formulations can be prepared by grinding together about 40% to 60% by weight of the formula I imidazolinyl benzoate, 2% to 3% by weight of the sodium salt of condensed naphthalene sulfonic acids, 2% to 3% by weight of a gelling clay, 2% by weight of propylene glycol, and from 54% to 32% by weight of water.

A typical granular formulation can be prepared by dissolving or dispersing the active compound in a solvent and applying the toxicant to a sorptive or nonsorptive carrier such as attapulgite, corn cob grits, pumice, talc, or the like.

The invention is further illustrated by the examples set forth below.

EXAMPLE 1

Preparation of 2-Propynyl o-(5-isopropyl-5-methyl-4-oxo-2-imidazolin-2-yl)benzoate To 12.5 ml of propargyl alcohol is added 0.1 g of a 50% suspension of sodium hydride in mineral oil. The addition is made under a blanket of nitrogen while the mixture is stirred and the temperature thereof maintained at from 20° C. to 25° C. by means of external cooling. The formation of the sodium salt of propargyl alcohol is complete in about 1 to 2 hours. To this solution is added 5.0 g of 3-isopropyl-3-methyl-5$\underline{H}$-imidazo[2,1-a]isoindole-2(3$\underline{H}$),5-dione and the mixture stirred at room temperature overnight under a blanket of nitrogen. Thin layer chromatography indicates incomplete reaction and an additional 50 mg of a 50% suspension of sodium hydride in oil is added to the reaction mixture. After stirring overnight, the mixture is cooled to 5° C. and 0.7 ml of 3N hydrochloric acid is added. The mixture is then diluted with methylene chloride, washed with water and the organic phase dried and concentrated in vacuo. The crystalline residue is transferred to a filter funnel with hexane and air dried to give 6.02 g of 2-propynyl o-(5-isopropyl-5-methyl-4-oxo-2-imidazolin-2-yl)benzoate, melting point 131°–144° C. Material from a similar reaction was recrystallized from acetonehexane to give pure product melting point 145°–147° C.

EXAMPLE 2

Preparation of Formula I Imidazolinyl Benzoates

The following imidazolinyl benzoates were prepared by essentially the same procedure as that described in Example 1, but substituting the appropriate alcohol for propargyl alcohol and the appropriate imidazoisoindoledione for 3-isopropyl-3methyl-5$\underline{H}$-imidazo[2,1-a]isoindole-2(3$\underline{H}$), 5-dione. Graphically, the reaction may be illustrated as follows:

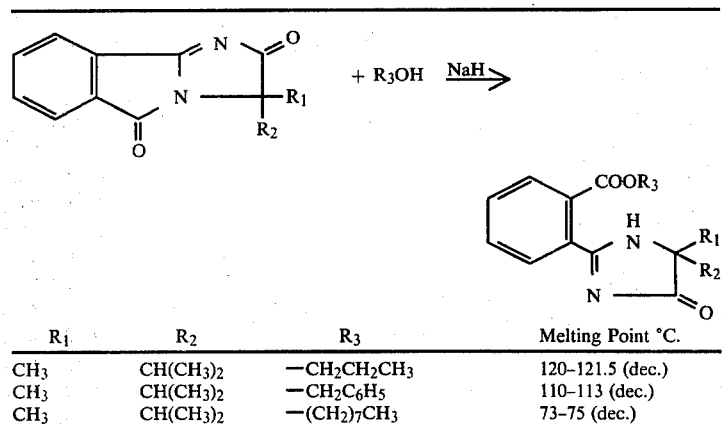

| $R_1$ | $R_2$ | $R_3$ | Melting Point °C. |
|---|---|---|---|
| CH$_3$ | CH(CH$_3$)$_2$ | —CH$_2$CH$_2$CH$_3$ | 120–121.5 (dec.) |
| CH$_3$ | CH(CH$_3$)$_2$ | —CH$_2$C$_6$H$_5$ | 110–113 (dec.) |
| CH$_3$ | CH(CH$_3$)$_2$ | —(CH$_2$)$_7$CH$_3$ | 73–75 (dec.) |

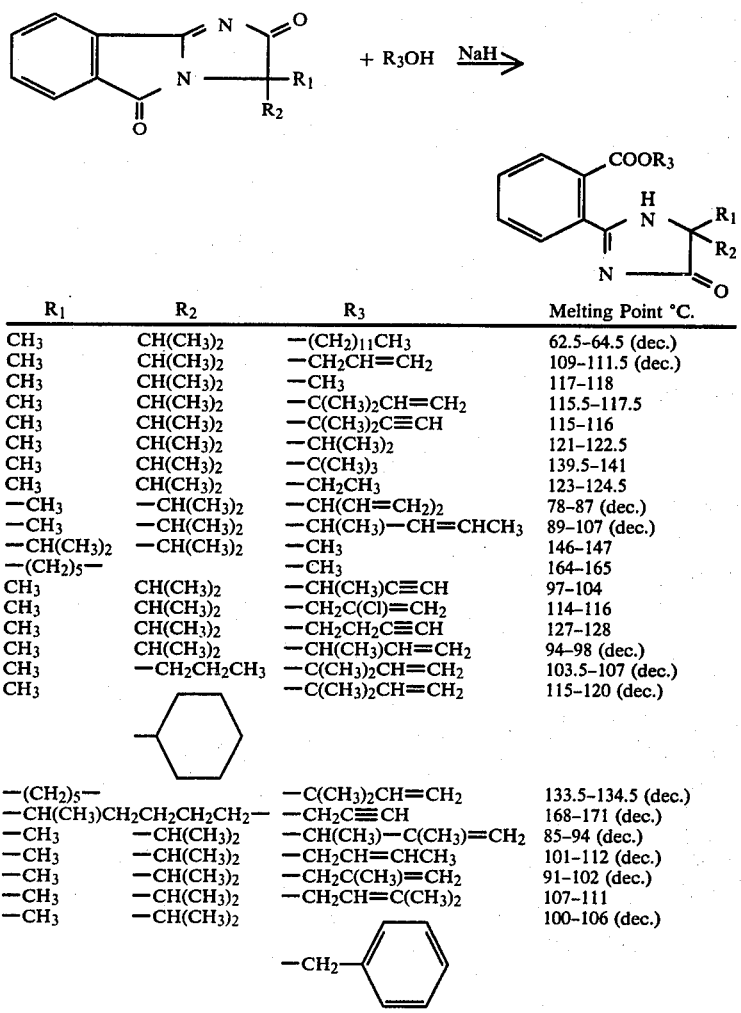

| R₁ | R₂ | R₃ | Melting Point °C. |
|---|---|---|---|
| CH₃ | CH(CH₃)₂ | —(CH₂)₁₁CH₃ | 62.5–64.5 (dec.) |
| CH₃ | CH(CH₃)₂ | —CH₂CH=CH₂ | 109–111.5 (dec.) |
| CH₃ | CH(CH₃)₂ | —CH₃ | 117–118 |
| CH₃ | CH(CH₃)₂ | —C(CH₃)₂CH=CH₂ | 115.5–117.5 |
| CH₃ | CH(CH₃)₂ | —C(CH₃)₂C≡CH | 115–116 |
| CH₃ | CH(CH₃)₂ | —CH(CH₃)₂ | 121–122.5 |
| CH₃ | CH(CH₃)₂ | —C(CH₃)₃ | 139.5–141 |
| CH₃ | CH(CH₃)₂ | —CH₂CH₃ | 123–124.5 |
| —CH₃ | —CH(CH₃)₂ | —CH(CH=CH₂)₂ | 78–87 (dec.) |
| —CH₃ | —CH(CH₃)₂ | —CH(CH₃)—CH=CHCH₃ | 89–107 (dec.) |
| —CH(CH₃)₂ | —CH(CH₃)₂ | —CH₃ | 146–147 |
| —(CH₂)₅— | | —CH₃ | 164–165 |
| CH₃ | CH(CH₃)₂ | —CH(CH₃)C≡CH | 97–104 |
| CH₃ | CH(CH₃)₂ | —CH₂C(Cl)=CH₂ | 114–116 |
| CH₃ | CH(CH₃)₂ | —CH₂CH₂C≡CH | 127–128 |
| CH₃ | CH(CH₃)₂ | —CH(CH₃)CH=CH₂ | 94–98 (dec.) |
| CH₃ | —CH₂CH₂CH₃ | —C(CH₃)₂CH=CH₂ | 103.5–107 (dec.) |
| CH₃ | cyclohexyl | —C(CH₃)₂CH=CH₂ | 115–120 (dec.) |
| —(CH₂)₅— | | —C(CH₃)₂CH=CH₂ | 133.5–134.5 (dec.) |
| —CH(CH₃)CH₂CH₂CH₂CH₂— | | —CH₂C≡CH | 168–171 (dec.) |
| —CH₃ | —CH(CH₃)₂ | —CH(CH₃)—C(CH₃)=CH₂ | 85–94 (dec.) |
| —CH₃ | —CH(CH₃)₂ | —CH₂CH=CHCH₃ | 101–112 (dec.) |
| —CH₃ | —CH(CH₃)₂ | —CH₂C(CH₃)=CH₂ | 91–102 (dec.) |
| —CH₃ | —CH(CH₃)₂ | —CH₂CH=C(CH₃)₂ | 107–111 |
| —CH₃ | —CH(CH₃)₂ | —CH₂-phenyl | 100–106 (dec.) |

EXAMPLE 3

Preparation of 1,1-Dimethylallyl o-(5-isopropyl-5-methyl-4-oxo-2-imidazoline-2-yl)benzoate hydrochloride To a solution containing 164 mg, 1,1-dimethylallyl o-(5-isopropyl-5-methyl-4-oxo-2-imidazolin-2-yl)benzoate (0.5 mmol) in 5 ml methylene chloride and 5 ml absolute ethanol is added 0.5 ml 1.0 N hydrochloric acid. The mixture is concentrated in vacuo and the residue treated with ether to give a crystalline product which is removed by filtration, washed with ether and air dried to give 170 mg hydrochloride salt, melting point 259°–262° C. (decomp.). The melting point of this and other salts is dependent upon the rate of heating.

EXAMPLE 4

Plant Growth Regulating Effect of Test Compounds Applied to the Foliage of Plants To evaluate test compounds as plant growth regulating agents, effective for reducing the relative stem growth of barley, said compounds are dissolved or dispersed in 50/50 aqueous/acetone mixtures and applied to the foliage of seedling plants growing in individual cups about 7.5 cm². A sufficient amount of a spreader-sticker is added to the mixture to provide approximately 0.1% by weight thereof in the mixture. The principal functioning agents of the spreader-sticker used are: alkylarylpolyethoxy ethanol, free and combined fatty acids, glycol ethers (di-alkyl), benzenedicarboxylate and isopropanol. This spreader-sticker has a specific gravity, of 0.90 at 20/20° C.; a density of 898.5 g/l at 20° C.; a Surface Tension of 30 dynes/cm at 0.1% concentration in H₂O; and a ph of 6±0.5 as a liquid spray film. It is marketed as BIO-FILM^R by Colloidal Products Corp. of Sausolito, California.

Treatment consists of spraying the test compound in acetone:water (1.1) at the rate of 747 liters per hectare on seedling barley plants, with a nozzle moving at a constant speed along a stationary track over the plants. In these tests, compound is applied at rates of from 0.11 to 4.48 kg per hectare.

The treated plants are placed on greenhouse benches and watered and fertilized in accordance with normal greenhouse procedures.

Three weeks after treatment plants in all treatment groups are measured and in some instances harvested and weighed. The height of control plants and treated plants are recorded and reported in Table I below.

The variety of barley used in the several tests are listed below along with their abbreviation.

| Barley Variety | Abbreviation |
|---|---|
| Villa | V |
| Mexico | M |
| Larker | L |
| Conquest | C |
| Trial | T |
| Early | E |
| Mona | Mo |

Dwarfing of all barley varieties treated is demonstrated in Table I below.

Table I

Evaluation of Imidazolinyl Benzoate Compounds having the Structure:

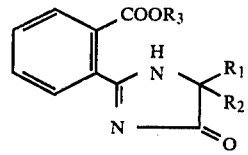

For Reducing The Relative Stem Growth of Barley.

| Structure | | | Rate | Barley | | |
|---|---|---|---|---|---|---|
| $R_1$ | $R_2$ | $R_3$ | kg/hectare | Variety | Ht. Cm. | Wt. gm. |
| | | Control | | V | 20.7 | 16.2 |
| $CH_3$ | $-CH(CH_3)_2$ | $-CH_2-\phi$ | 4.48 | | 16.7 | 16.1 |
| | | | 2.24 | V | 13.5 | 15.3 |
| | | | 0.56 | | 13.5 | 15.3 |
| | | | 4.48 | | 18.5 | 16 |
| $CH_3$ | $-CH(CH_3)_2$ | $-(CH_2)_7CH_3$ | 2.24 | V | 19.5 | 17.3 |
| | | | 0.56 | | 19.7 | 17.1 |
| | | Control | | V | 11.7 | 16.2 |
| | | | 3.36 | | 9.3 | 15.1 |
| $CH_3$ | $-CH(CH_3)_2$ | $-CH_2CH_2CH_3$ | 1.12 | V | 11.0 | 15.2 |
| | | | 0.33 | | 12.0 | 14.6 |
| | | Control | | | 18.0 | 15.1 |
| | | | 2.24 | | 14.3 | 14.9 |
| $CH_3$ | $-CH(CH_3)_2$ | $-CH_2-CH=CH_2$ | 0.44 | V | 14.8 | 16.2 |
| | | | 0.11 | | 14.8 | 13.8 |
| | | Control | | | 20.9 | 19.9 |
| | | | 1.12 | | toxic | toxic |
| $CH_3$ | $-CH(CH_3)_2$ | $-CH_2C\equiv CH$ | 0.28 | V | 11.0 | 13.8 |
| | | | 0.06 | | 18.2 | 17.7 |
| | | Control | | L | 28.6 | |
| | | | 3.36 | | 27.2 | |
| $CH_3$ | $-CH(CH_3)_2$ | $-CH_2CH_2C\equiv CH$ | 2.24 | L | 27.0 | |
| | | | 1.12 | | 28.2 | |
| | | | 2.24 | | 26.4 | |
| $CH_3$ | $-CH(CH_3)_2$ | $-CH_2-\phi$ | 1.12 | L | 29.0 | |
| | | | 0.56 | | 28.0 | |
| | | | 2.24 | | 26.6 | |
| $CH_3$ | $-CH(CH_3)_2$ | $-CH_2CH=CHCH_3$ | 1.12 | L | 26.6 | |
| | | | 0.56 | | 28.0 | |
| | | | 0.22 | | 23.6 | |
| $CH_3$ | $-CH(CH_3)_2$ | $-CH(CH=CH_2)_2$ | 0.11 | L | 26.0 | |
| | | | 0.06 | | 26.6 | |
| | | Control | | L | 28.5 | |
| | | | 3.36 | | 25.2 | |
| $CH_3$ | $-CH(CH_3)_2$ | $-CH(CH_3)_2$ | 2.24 | L | 26.8 | |
| | | | 1.10 | | 25.0 | |
| | | | 3.36 | | 26.8 | |
| $CH_3$ | $-CH(CH_3)_2$ | $-C(CH_3)_2C\equiv CH$ | 2.24 | L | 26.8 | |
| | | | 1.10 | | 28.6 | |
| | | Control | | L | 33.0 | |
| | | $\overset{CH_3}{\underset{-CHCH=CHCH_3}{\mid}}$ | 2.24 | | 25 | |
| $CH_3$ | $-CH(CH_3)_2$ | | 0.56 | L | 29.6 | |
| | | | 0.11 | | 32.2 | |
| | | Control | | M | 30.0 | |
| | | Control | | C | 25.8 | |
| | | Control | | T | 28.5 | |
| | | Control | | Mo | 29.5 | |
| | | Control | | E | 25.5 | |
| | | $\overset{CH_3}{\underset{-CHC\equiv CH}{\mid}}$ | 1.65 | | 29.3 | |
| $CH_3$ | $-CH(CH_3)_2$ | | 0.65 | M | 28.8 | |
| | | | 0.28 | | 30.3 | |

Table I-continued

Evaluation of Imidazolinyl Benzoate Compounds having the Structure:

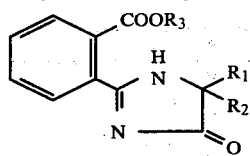

For Reducing The Relative Stem Growth of Barley.

| R₁ | R₂ | R₃ | Rate kg/hectare | Variety | Barley Ht. Cm. | Wt. gm. |
|---|---|---|---|---|---|---|
| CH₃ | —CH(CH₃)₂ | CH₃<br>\|<br>—CHC=CH | 1.65<br>0.56<br>0.28 | C | 22.8<br>23.3<br>24.3 | |
| CH₃ | —CH(CH₃)₂ | CH₃<br>\|<br>—CHC≡CH | 1.65<br>0.56<br>0.28 | T | 25.8<br>28.8<br>26.3 | |
| CH₃ | —CH(CH₃)₂ | CH₃<br>\|<br>—CHC≡CH | 1.65<br>0.56<br>0.28 | Mo | 11.9<br>5.8<br>4.1 | |
| CH₃ | —CH(CH₃)₂ | CH₃<br>\|<br>—CHC≡CH | 1.65<br>0.56<br>0.28 | E | 21.3<br>22.5<br>25.8 | |

EXAMPLE 5

Evaluation of Imidazolinyl Benzoates for Reducing The Relative Stem Growth of Corn and Snapbeans Following the procedure of Example 4, but substituting corn and snapbeans for barley, demonstrates the effectiveness of the imidazolinyl benzoates for reducing the relative stem growth on said corn and snapbeans.

The variety of snapbeans used in these tests is Greensleeves and the corn is Field Corn FR 619.

barley and Fiskby V Soybeans. Also, rather than recording report exact measurements, plants are rated according to the following Index.

| | % Change in Fresh or Dry Weight or Height | |
|---|---|---|
| 1. | 50% | Decrease |
| 2. | 35–50% | Decrease |
| 3. | 20–34% | Decrease |
| 4. | 1–19% | Decrease |
| 5. | 0–10% | Increase |

Table II

Evaluation of Imidazolinyl Benzoates having the Structure:

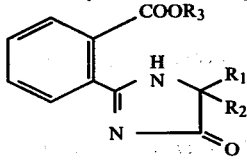

For Reducing the Relative Stem Growth of Corn and Snapbeans.

| R₁ | R₂ | R₃ | Rate kg/hectare | Corn Ht. Cm. | Wt. gm. | Snapbeans Ht. Cm. | Wt. gm. |
|---|---|---|---|---|---|---|---|
| | Control | | | 77.6 | 18.3 | 32.7 | 27.0 |
| CH₃ | —CH(CH₃)₂ | —CH₂-φ | 2.24<br>0.56<br>0.11 | 50.8<br>57.2<br>46.2 | 11.1<br>13.3<br>11.6 | 24.2<br>22.4<br>16.2 | 14.6<br>15.2<br>9.1 |
| CH₃ | —CH(CH₃)₂ | —(CH₂)₇CH₃ | 2.24<br>0.56<br>0.11 | 61.4<br>71.2<br>80.6 | 12.8<br>15.6<br>22.2 | 21.0<br>30.4<br>27.6 | 13.3<br>24.4<br>24.5 |
| | Control | | | 78.9 | 23.8 | 36.8 | 22.4 |
| CH₃ | —CH(CH₃)₂ | —CH₂CH₂CH₃ | 1.65<br>0.44<br>0.09 | 41.2<br>59.8<br>63.0 | 11.1<br>16.6<br>19.1 | 19.6<br>15.6<br>18.6 | 9.6<br>10.4<br>9.4 |
| | Control | | | 49.8 | 15.5 | 30.9 | 25.2 |
| CH₃ | —CH(CH₃)₂ | —CH₂—CH=CH₂ | 2.24<br>0.44<br>0.11 | toxic<br>18.4<br>26.4 | toxic<br>4.1<br>7.2 | toxic<br>17.6<br>19.2 | toxic<br>9.0<br>12.4 |
| | Control | | | 77.6 | 18.3 | 32.7 | 27.0 |
| CH₃ | —CH(CH₃)₂ | —C₈H₁₇-n | 2.24<br>0.56<br>0.11 | 61.4<br>71.2<br>80.6 | 12.8<br>15.6<br>22.2 | 21.0<br>30.4<br>27.6 | 13.3<br>24.4<br>24.5 |

EXAMPLE 6

Evaluation of Imidazolinyl Benzoates for Reducing The Relative Stem Growth of Barley and Soybeans The evaluation procedure employed in the following tests is essentially the same as that described in Example 4 above. However, the plant species used are Larker Data obtained in these tests are reported in Table III below.

Table III

Evaluation of Imidazolinyl Benzoates having the Structure:

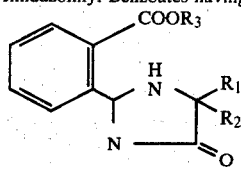

For Reducing The Relative Stem Growth of Barley and Soybeans.

| $R_1$ | $R_2$ | $R_3$ | Rate kg/hectare | Height Barley | Reduction Soybeans |
|---|---|---|---|---|---|
| CH₃ | —CH(CH₃)₂ | —CH₂C≡CH (Cl) | 1.12 | 1 | 1 |
| | | | 0.44 | 1 | 1 |
| | | | 0.22 | — | 1 |
| CH₃ | —CH(CH₃)₂ | —C(CH₃)₂CH=CH₂ | 0.11 | 2 | — |
| | | | 0.033 | 5 | — |
| | | | 0.011 | — | 3 |
| | | | 0.025 | — | 4 |
| | | | 0.56 | — | 3 |
| CH₃ | —CH(CH₃)₂ | —C₂H₅ | 0.11 | — | 3 |
| | | | 0.03 | — | 4 |
| | | | 0.28 | — | 2 |
| CH₃ | —CH(CH₃)₂ | C(CH₃)₂C≡CH | 0.05 | — | 3 |
| CH₃ | —CH(CH₃)₂ | —CHCH=CHCH₃ (CH₃) | 0.56 | — | 2 |
| | | | 0.11 | — | 3 |
| CH₃ | —CH(CH₃)₂ | —CH₂CH₂C≡CH | 1.12 | 3 | 2 |
| | | | 0.22 | 4 | 3 |
| | | | 0.04 | — | 4 |
| CH₃ | —CH(CH₃)₂ | —CH₂CH=C(CH₃)₂ | 1.12 | 1 | 2 |
| | | | 0.02 | 4 | 3 |
| | | | 0.04 | — | 4 |
| CH₃ | —CH(CH₃)₂ | —CH₂-⟨cyclohexenyl⟩ | 1.12 | — | 3 |
| | | | 0.02 | — | 3 |
| | | | 0.04 | — | 3 |
| CH₃ | —CH(CH₃)₂ | —CH₂CH=CHCH₃ | 1.11 | 1 | 2 |
| | | | 0.22 | 4 | — |
| | | | 0.04 | — | — |
| CH₃ | —CH(CH₃)₂ | —C(CH₃)₂CH=CH₂ . HCl | 0.56 | — | 1 |
| | | | 0.11 | 3 | 2 |
| | | | 0.025 | — | 4 |
| CH₃ | —CH(CH₃)₂ | C(CH₃)₂C≡CH | 2.24 | 2 | 2 |
| | | | 0.56 | 4 | 3 |
| | | | 0.11 | — | 4 |
| | ⟨cyclohexyl⟩ | —C(CH₃)₂CH=CH₂ | 1.12 | 1 | — |
| | | | 0.22 | 3 | — |
| | | | 0.04 | — | — |
| CH₃ | —CH(CH₃)₂ | CH(CH₃)C≡CH | 1.12 | 1 | — |
| | | | 0.22 | 3 | — |
| | | | 0.04 | — | — |

EXAMPLE 7

"Snap Test" Field Trials

In order to determine whether the stems of graminaceous plants have been strengthened by treatment with test compounds, a handful of culms (stems) of the treated plants are pushed sideways from a point just below the seed heads to an angle of about 45° and then released. This procedure is repeated six times per plot. The force required to push the stems over and the speed and force with which they "snap" back to the verticle position is measured. The rating is based on feel only and thus is relative. A scale of 1 to 5 is used with a rating of 1 indicating the weakest stems and a rating of 5 indicating the most rigid stems. The test is performed at the full heading stage of the crop. In this test the crop used is barley and the variety used is Villa. Data obtained are reported in Table IV below.

Table IV

Snap Test on Barley Plants

| Compound | Rate kg/hectare | Average Height(Cm) | Average Snap test Rating |
|---|---|---|---|
| o -(5-isopropyl-5-methyl -4-oxo-2-imidazolin-2-yl) -benzoic acid, benzyl ester | 0.56 | 62.2 | 3.16 |
| | 1.12 | 60.5 | 3.33 |
| | 3.36 | 56.6 | 4.00 |
| | 0.56 | 62.2 | 3.40 |
| | 1.65 | 59.9 | 3.08 |
| | 3.36 | 62.2 | 3.50 |
| Controls | — | 62.7 | 3.10 |

EXAMPLE 8

Bud inhibition on young potted coffee plants is demonstrated in the following tests wherein the trunks of young potted coffee plants are sprayed with an aqueous dispersion of the emulsifiable concentrate referred to in Example 9 below. Eight plants per treatment were used and each plant was treated with about 25; 50 or 100 mg of test compound. One hundred seven days after treatment the plants were examined and the average number of axillary sprouts and average sprout size recorded. Data obtained are reported in Table V below.

Table V

Bud Inhibition on Coffee Plants

| Compound | Rate mg/plant | Sprouts Average No. per plant | Average size cm. |
|---|---|---|---|
| 2-propynyl 0(5-isopropyl | 105 | 0 | — |
| -5-methyl-4-oxo-2- | 52.25 | 3 | 0.1 |
| imidazolin-2-yl)benzoic | 26.12 | 4 | 0.3 |
| Untreated Controls | — | 4 | 10.0 |

EXAMPLE 9

To evaluate the compounds of the subject invention for decreasing the number of developing buds on coffee trees, an aqueous dispersion of a two pound per gallon emulsifiable concentrate is prepared by dispersing 25% by weight of 2-propynyl 0(5-isopropyl-5-methyl-(4-oxo-2-imidazolin-2-yl) benzoic acid, methyl ester in, 50% by weight of cyclohexanone, 15% by weight of a heavy aromatic solvent (Hi Sol) and 10% by weight of a non-ionic emulsifier (T Mulz 339). The emulsifiable concentrate is dispersed in water in a sufficient amount to provide 2000 mg. of active compound per 90 ml of water. The trunks of fifteen year old Mundo novo coffee plants were prunned to 0.6 m from the soil and one out of two trunks per hill treated with 90 ml of test solution per trunk. This equals 2.860 kg/hectare of the active compound.

Sixty days after treatment the trunks of the coffee trees were examined and the average number and size (cm) of the sprouts recorded.

In these tests the untreated trunks averaged 15.3 sprouts measuring 3.7 cm; whereas the treated trunks had an average 4.3 sprouts per trunk measuring 2.1 cm.

EXAMPLE 10

Further evaluation of the compounds of the present invention as axillary bud growth inhibitors on tobacco plants is undertaken in the following test.

In these tests 10 mg of test compound are dispersed or dissolved in 200 ml of a 50/50 acetone/water mixture. Eight week old tobacco plants are mechanically topped and then each plant is sprayed with 40 ml of test solution containing 2 mg. of active ingredient. The treated plants are placed on greenhouse benches and cared for in accordance with normal greenhouse procedures. Three weeks after treatment all plants (five per treatment) are examined and number of suckers per plant determined. Data obtained are reported in Table VI below.

Table VI

Axillary Growth Inhibition on Tobacco

| Compound | Avg. No. Suckers Per Plant | Percent Bud Growth Inhibition |
|---|---|---|
| Control (untreated | 19.4 | — |
| 0-(5-isopropyl-5-methyl-4-oxo-2-imidazolin-2-yl)benzoic acid, benzyl ester | 18.2 | 6.2 |
| 0-(5-isopropyl-5-methyl-4-oxo-2-imidazolin-2-yl)-benzoic acid, 2-propynyl ester | 0.6 | 96.9 |

EXAMPLE 11

Evaluation of the compounds of the present invention as axillary growth inhibitors on tobacco plants is undertaken in the following test.

In this test 6 week old Xanthia tobacco plants are topped and then sprayed with 30 ml of a 50/50 acetone/water mixture containing from 1 to 5 mg of test compound. Untreated topped tobacco plants are used as controls. Three weeks after spraying the suckers on all plants are counted and then removed and weighed. Five plants per treatment are employed and the results averaged. Results obtained are reported in Table VII below.

Table VII

Tobacco Bud Inhibition

| Compound | Rate mg/plant | Avg. No. of Suckers | Avg. wt (g) of Suckers | % Control |
|---|---|---|---|---|
| 0-(5-Isopropyl-5-methyl-4-oxo-2-imidazolin-2-yl)benzoic acid, methyl ester | 5 | 4 | 1.6 | 85 |
| | 2.5 | 2 | 10.3 | 4.2 |
| 0-(5-Isopropyl-5-methyl-4-oxo-2-imidazolin-2-yl)benzoic acid, 2-propynyl esters | 2 | 4 | 1.9 | 82.3 |
| | 1 | 2.5 | 6.4 | 40.5 |
| Checks | — | 2 | 10.75 | — |

What is claimed is:

1. A method for controlling the relative stem growth of plants comprising applying to the foliage, stems, roots or seeds of said plants or to soil in which said plants are grown, a plant growth regulating amount of a compound having the formula:

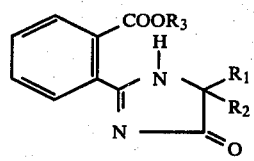

wherein $R_1$ is methyl; $R_2$ is isopropyl; $R_3$ is alkyl $C_1$–$C_{12}$, alkenyl $C_3$–$C_5$ optionally substituted with one chlorine or one or two methyl substituents, alkynyl $C_3$–$C_5$ optionally substituted with methyl, benzyl, cyclohexenylmethyl, or pentadienyl; and the acid addition salts thereof.

2. A method according to claim 1 wherein the plants are crop plants selected from the group consisting of graminaceous crops, bean producing legumes, solenaceous plants and woody plant species.

3. A method according to claim 2 wherein the compound is o-(5-isopropyl-5-methyl-4-oxo-2-imidazolin-2-yl)-benzoic acid, 1-methyl-2-propynyl ester.

4. A method according to claim 2 wherein the compound is o-(5-isopropyl-5-methyl-4-oxo-2-imidazolin-2-yl)-benzoic acid 3-methyl-2-butenyl ester.

5. A method according to claim 2 wherein the compound is o-(5-isopropyl-5-methyl-4-oxo-2-imidazolin-2-yl)-benzoic acid, 3-butynyl ester.

6. A method according to claim 2 wherein the compound is O-(5-isopropyl-5-methyl-4-oxo-2-imidazolin-2-yl)benzoic acid, 2-propynyl ester.

7. A method according to claim 2 wherein the compound is o-(5-isopropyl-5-methyl-4-oxo-2-imidazolin-2-yl)benzoic acid, 2-butenyl ester.

8. A method according to claim 2 wherein the compound is o-(5-isopropyl-5-methyl-4-oxo-2-imidazolin-2-yl)benzoic acid, 1-methyl-2-butenyl ester.

9. A method according to claim 1 for reducing the relative stem growth for graminaceous crops and bean producing legumes by applying the compound to the foliage, stems, roots or seeds of said plants or to soil in which said plants are grown at a rate of about 0.0002 to 4.48 kg/hectare.

* * * * *

Disclaimer 4,170,462.—*Thomas Denny O'Neal*, Princeton, N.J. METHOD FOR CONTROLLING THE RELATIVE STEM GROWTH OF PLANTS. Patent dated Oct. 9, 1979. Disclaimer filed Feb. 19, 1981, by the assignee, *American Cyanamid Co.*

Hereby enters this disclaimer to claims 1-9 of said patent.
[*Official Gazette April 28, 1981.*]